US009297696B2

(12) United States Patent
Woodruff et al.

(10) Patent No.: US 9,297,696 B2
(45) Date of Patent: Mar. 29, 2016

(54) LASER BASED ANALYSIS USING A PASSIVELY Q-SWITCHED LASER EMPLOYING ANALYSIS ELECTRONICS AND A MEANS FOR DETECTING ATOMIC OPTICAL EMISSION OF THE LASER MEDIA (71) Applicants: Steven D Woodruff, Morgantown, WV (US); Dustin L. Mcintyre, Washington, PA (US)

(72) Inventors: Steven D Woodruff, Morgantown, WV (US); Dustin L. Mcintyre, Washington, PA (US)

(73) Assignee: U.S. Department of Energy, Washington, DC (US)

( * ) Notice: Subject to any disclaimer, the term of this patent is extended or adjusted under 35 U.S.C. 154(b) by 306 days.

(21) Appl. No.: 13/749,842

(22) Filed: Jan. 25, 2013

(65) Prior Publication Data
US 2014/0209794 A1 Jul. 31, 2014

(51) Int. Cl.
*H01J 3/14* (2006.01)
*G01J 3/50* (2006.01)
*G01J 3/443* (2006.01)
*G01N 21/71* (2006.01)
*G01N 21/64* (2006.01)
*G01N 21/65* (2006.01)

(52) U.S. Cl.
CPC .............. *G01J 3/443* (2013.01); *G01N 21/718* (2013.01); *G01N 21/6402* (2013.01); *G01N 21/65* (2013.01)

(58) Field of Classification Search
CPC .............. G01J 1/42; H01S 3/11; H01L 21/20

USPC ....... 250/226, 216, 214 SW, 205, 214 R, 551; 372/9–17, 38.1, 38.03, 69–80, 109; 356/3, 300, 302, 303, 319, 326
See application file for complete search history.

(56) References Cited

U.S. PATENT DOCUMENTS

| 4,884,275 | A | 11/1989 | Simms |
| 7,394,537 | B1 | 7/2008 | Lindfors et al. |
| 7,421,166 | B1 * | 9/2008 | Woodruff et al. ............... 385/39 |
| 8,125,627 | B2 | 2/2012 | Dottery et al. |
| 2006/0159132 | A1 * | 7/2006 | Young et al. .................... 372/10 |
| 2008/0151241 | A1 * | 6/2008 | Lindfors et al. .............. 356/318 |

OTHER PUBLICATIONS

Jeffrey A. Morris and Clifford R. Pollock, Passive Q switching of a diode-pumped Nd:YAG laser with a saturable absorber, Apr. 15, 1990, vol. 15 (8), Optics Letters, pp. 440-442.*
Lew Goldberg, Chris McIntosh, and Brian Cole, VCSEL end-pumped passively Q-switched Nd:YAG laser with adjustable pulse energy, Feb. 17, 2011, vol. 19 (5), Optics Express, pp. 4261-4267.*

* cited by examiner

*Primary Examiner* — Pascal M Bui Pho
(74) *Attorney, Agent, or Firm* — Jacob A. Heafner; Brian J. Lally; John T. Lucas (57) ABSTRACT

A device for Laser based Analysis using a Passively Q-Switched Laser comprising an optical pumping source optically connected to a laser media. The laser media and a Q-switch are positioned between and optically connected to a high reflectivity mirror (HR) and an output coupler (OC) along an optical axis. The output coupler (OC) is optically connected to the output lens along the optical axis. A means for detecting atomic optical emission comprises a filter and a light detector. The optical filter is optically connected to the laser media and the optical detector. A control system is connected to the optical detector and the analysis electronics. The analysis electronics are optically connected to the output lens. The detection of the large scale laser output production triggers the control system to initiate the precise timing and data collection from the detector and analysis.

19 Claims, 9 Drawing Sheets

LASER BASED ANALYSIS USING A PASSIVELY Q-SWITCHED LASER EMPLOYING ANALYSIS ELECTRONICS AND A MEANS FOR DETECTING ATOMIC OPTICAL EMISSION OF THE LASER MEDIA

GOVERNMENT INTERESTS

The United States Government has rights in this invention pursuant to the employer/employee relationship between the inventors and the U.S. Department of Energy, operators of the National Energy Technology Laboratory (NETL).

FIELD OF THE INVENTION

The present invention relates to the use of a passively Q-switched laser in analysis using precision timing as described herein. Preferably the analysis is Laser Induced Breakdown Spectroscopy (LIBS).

BACKGROUND OF THE INVENTION

Current light based analysis requires the use of expensive equipment that offers a complicated system that is difficult to maintain. Although laser induced breakdown spectroscopy (LIBS) offers a low cost analysis system, it is plagued by its requirements for precise control of laser pulses in conjunction with precise timing of the optical spectrometer. Generally, LIBS systems use actively Q-switched lasers, due to their precision timing. In an actively Q-switched laser an input signal is used to control the laser output and to time the measurement. Passively Q-switched lasers do not have a highly precise timing signal, making them unsuitable for LIBS to those in the art. Therefore, there is a need in the art for a low cost, reliable, laser based analysis using a passively q-switched laser.

SUMMARY OF THE INVENTION

A device for laser based analysis using a passively Q-Switched laser comprising an optical pumping source, a high reflectivity mirror (HR), a laser media, a Q-switch, an output coupler (OC) an output lens, a means for detecting atomic optical emission of the laser media, a control system, and analysis electronics. The high reflectivity mirror (HR), the laser media, the Q-switch, the output coupler (OC) and the output lens are positioned along an optical axis. The optical pumping source is optically connected to the laser media preferably by being focused along the optical axis, or from the side focused onto the optical axis. The optical pumping source creates a pumping excitation energy for the laser media. The laser media is made of a material that emits an atomic optical emission when exposed to the pumping excitation energy. The high reflectivity mirror (HR) is reflective to the atomic optical emission of the laser media. The laser media and the Q-switch are positioned between and optically connected to the high reflectivity mirror (HR) and the output coupler (OC) along the optical axis. In one embodiment, the laser media and the Q-switch are fused to be a single element and the high reflectivity mirror (HR) and the output coupler (OC) are preferably coatings on either end of the composite media/Q-switch. The output coupler (OC) is optically connected to the output lens along the optical axis. The means for detecting atomic optical emission of the laser media comprises a filter and a light detector. The optical filter optically connects the optical detector to the atomic optical emission of the laser media, while also filtering at least a portion of said pumping excitation energy from reaching the optical detector. Therefore, only atomic optical lasing emission of the laser media reaching the optical detector pass through the optical filter.

The optical filter is optically connected to the laser media and the optical detector. The control system is connected to the optical detector and the analysis electronics. The analysis electronics are optically connected to the output of the output lens.

DETAILED DESCRIPTION OF THE INVENTION

Figure 1:
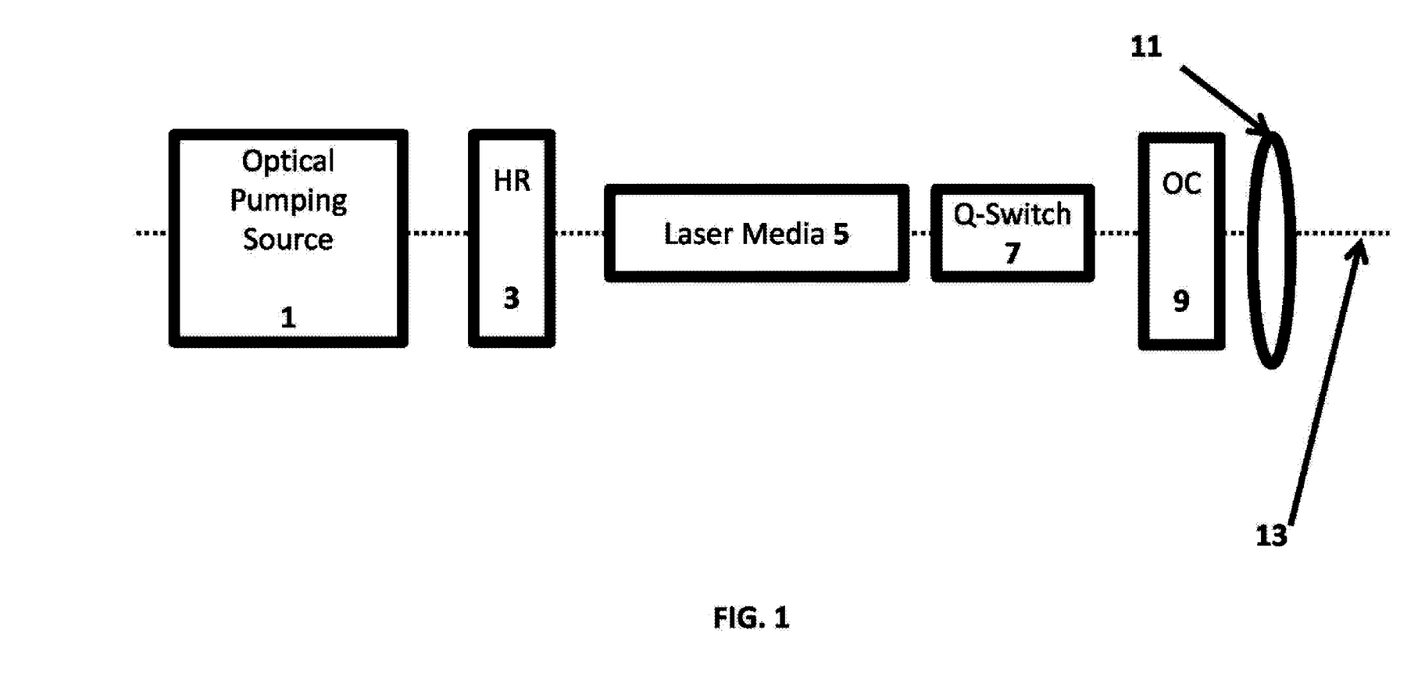
FIG. 1 depicts an overview of one embodiment of a device for Laser Based Analysis using a Passively Q-Switched Laser.

FIG. 1 depicts an overview of one embodiment of a device for Laser based Analysis using a Passively Q-Switched Laser. As shown an optical pumping source 1, a high reflectivity mirror (HR) 3, a laser media 5, a Q-switch 7, an output coupler (OC) 9 and an output lens 11 are positioned along an optical axis 13. The optical pumping source 1 is optically connected to the laser media 5. The laser media 5 and the Q-switch 7 are positioned between and optically connected to the high reflectivity mirror (HR) 3 and the output coupler (OC) 9 along the optical axis. A means for detecting atomic optical emission of the laser media, described below, comprises a filter and a light detector.

Figure 2:
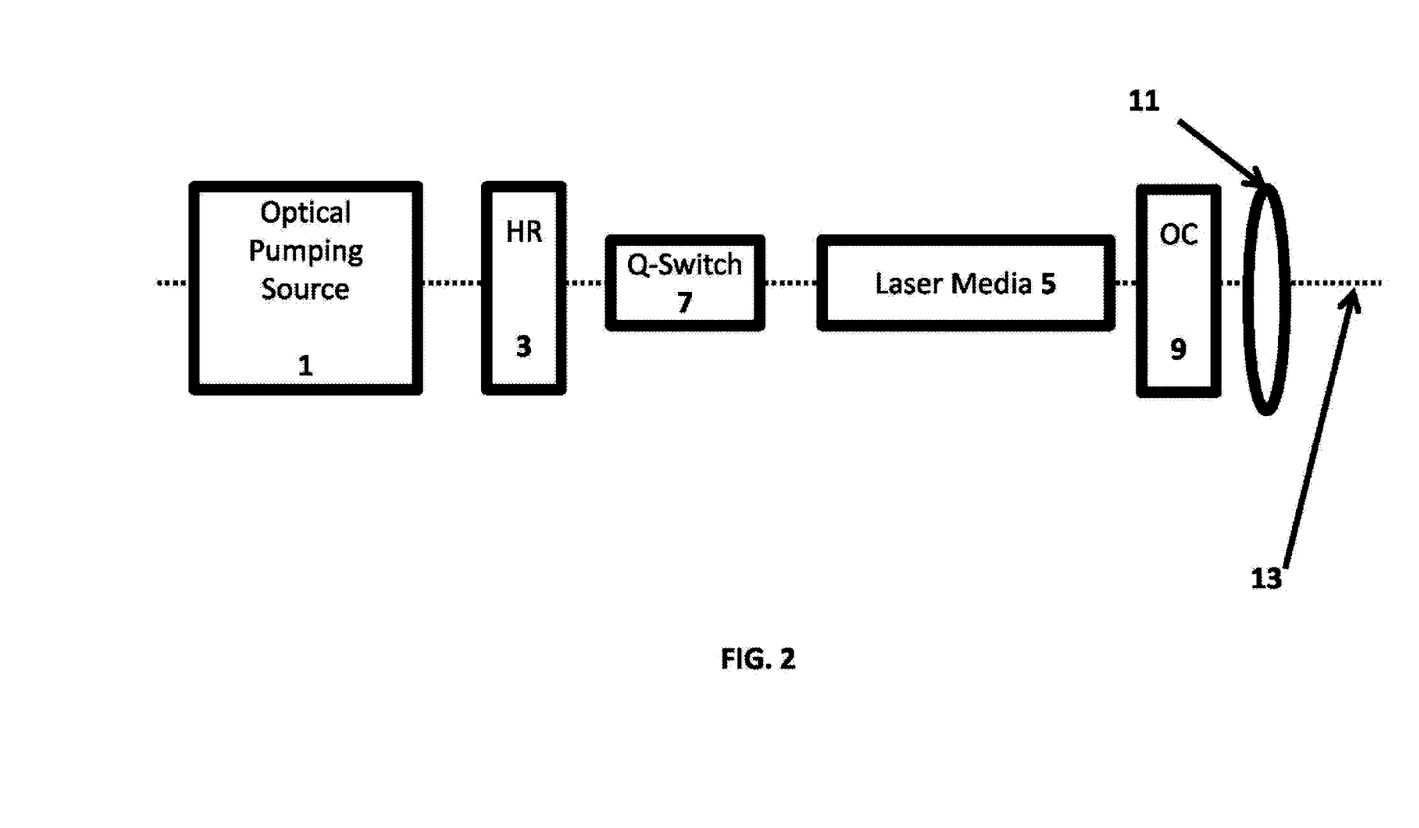
FIG. 2 depicts an overview of one embodiment of a device for Laser Based Analysis using a Passively Q-Switched Laser with an alternate positioning of the Q-switch.
Figure 3:
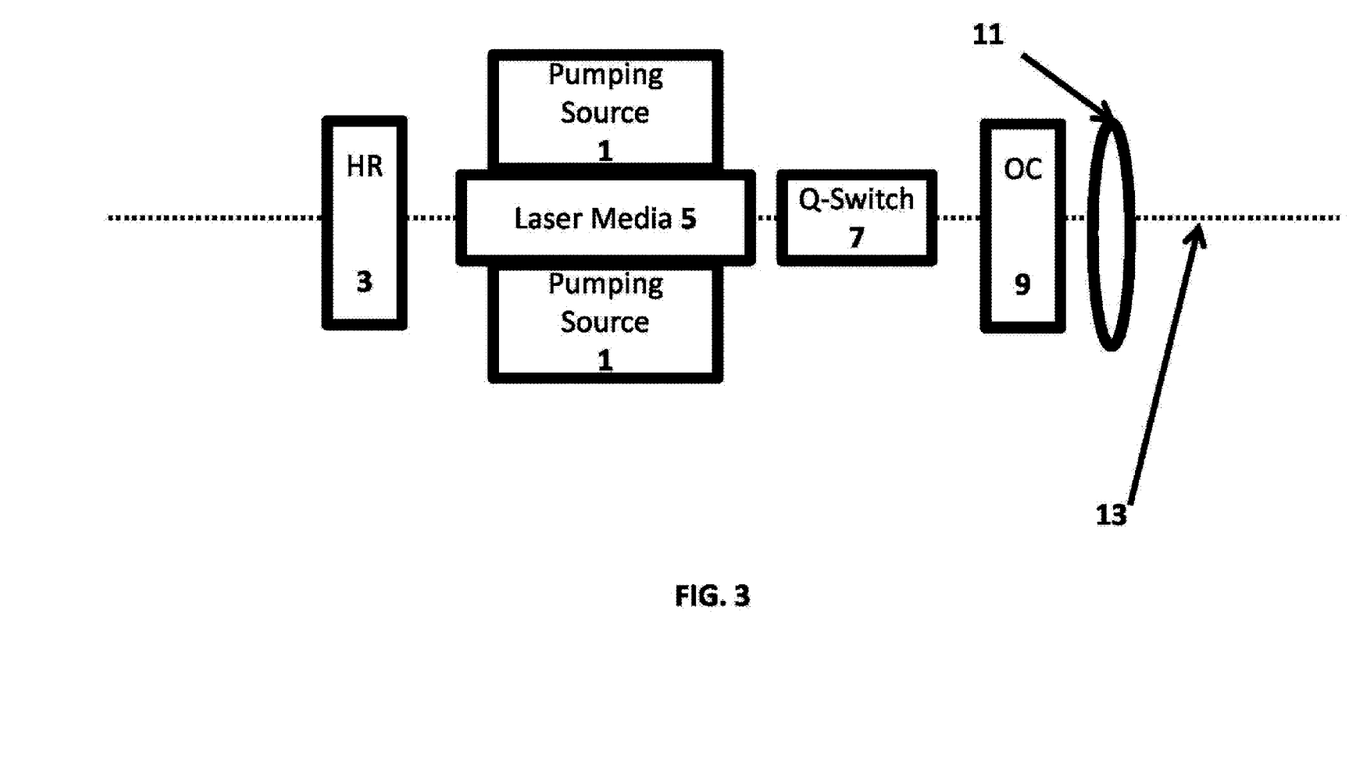
FIG. 3 depicts an overview of one embodiment of a device for Laser Based Analysis using a Side-pumped, Passively Q-Switched Laser.
Figure 4:
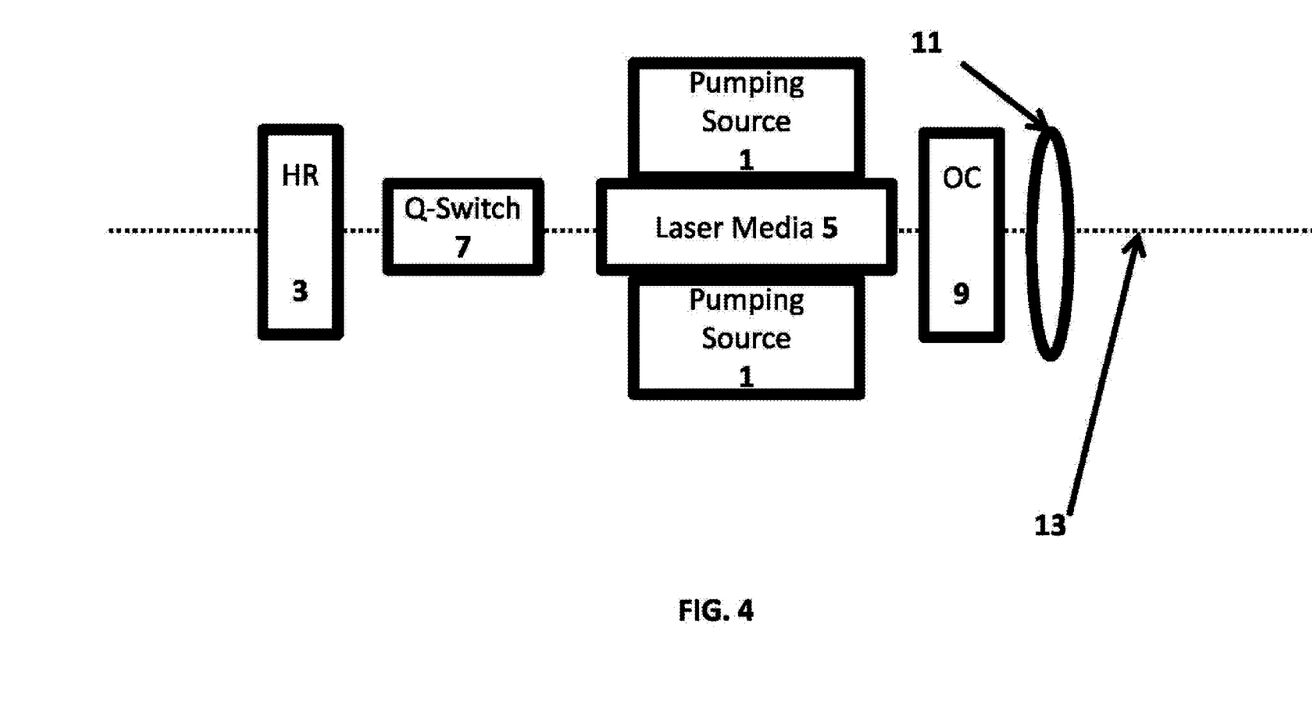
FIG. 4 depicts an overview of one embodiment of a device for Laser Based Analysis using a Side-pumped, Passively Q-Switched Laser with an alternate positioning of the Q-switch.

As used herein, the term optically connected shall refer to any means of optically transferring between either directly or through any number of intermediate components. For example the optical pumping source 1 optically connected to the laser media 5 refers to a direct connection as shown in FIG. 3 and FIG. 4 or an indirect connection as shown in FIG. 1 or FIG. 2, whereby the pumping excitation energy from the optical pumping source 1 must first pass through a number of optical components before it reaches the laser media 5.

In a preferred embodiment, the optical pumping excitation energy emitted from the optical pumping source 1 passes through the high reflectivity mirror (HR) 3, and excites the laser media 5. In this embodiment, the high reflectivity mirror (HR) 3 reflects light at the lasing wavelength and transmits light at the pumping wavelength. In another embodiment, the optical pumping excitation energy emitted from the optical pumping source 1 passes through the Q-switch 7 before it excites the laser media 5, for example, the embodiment shown in FIG. 2. The stored excited states of the laser media 5 spontaneously decay producing an atomic optical emission in random directions. The emission received at the output coupler (OC) 9 will be partially reflected back to the laser media 5. Preferably, the output coupler (OC) 9 will reflect less than 50% of the emission energy towards the laser media 5 along the optical axis. The output energy emitted from the laser media 5 towards the Q-switch 7 is partially absorbed by the Q-switch 7 to prevent lasing from occurring. The emission energy that is received at the high reflectivity mirror (HR) 3 is reflected back towards the laser media 5 along the optical axis 13.

The emission energy will reflect back and forth between the high reflectivity mirror (HR) 3, and the output coupler (OC) 9 along the optical axis. The emission energy will traverse the laser media 5 and interact with excited atoms, preferably Nd, within the laser media 5, inducing stimulated emission where the original photons from the emission energy cause the decay of an excited state. The stimulated event produces light of the same wavelength (about 1064 nm for a Nd:YAG laser media 5), phase, and in the same direction as the stimulating photon. At the same time the Q-switch 7 allows a certain percentage of the incident photons to pass through unimpeded. The balance of the certain percentage of photons is absorbed within the Q-switch 7 inducing excited states. When the material of the Q-switch 7 is in an excited state it is virtually transparent to the atomic optical emission of the laser media 5. Therefore as more of the emission energy is absorbed it effectively makes the Q-switch 7 more and more transparent for a short time. This allows more emission energy to pass through and return producing more stimulated emissions within the laser media 5.

This process of increasing the transparency of the Q switch 7 allows a large number of excited states to build up within the laser media 5 until the Q switch 7 reaches a threshold transparency. The Q switch 7 begins to increase transparency exponentially and the number of photons, induced from the emission energy, within the laser cavity (high reflectivity mirror (HR) 3, laser media 5, Q-switch 7, and output coupler (OC) 9) also grows exponentially. At this point, the Q-switch 7 is virtually clear of losses and large scale lasing occurs depleting the excited states in the laser media 5 within a few round trips. The output energy produced is a large number of photons in a very short pulse width. The laser output energy is directed through the output lens 11. The output lens 11 focuses the laser output energy. In one embodiment, the output lens 11 focuses the laser output energy down to a sufficiently small spot size, generating a power density or photon flux density of about $1 \times 10^{11}$ W/cm$^2$ or greater so as to create a spark.

The Optical Pumping Source 1

The optical pumping source 1 creates an optical pumping excitation energy having low peak power, preferably less than 1,000 peak Watts, more preferably about 100-1,000 Watts, depending on the material of the laser media 5. The optical pumping excitation energy needs to be sufficient enough to excite the laser media 5 at a greater rate than lost from subsequent stimulated emission and/or natural decay. The optical pumping excitation energy may be a single pulse, a continuous stream, or a series of pulses. In the preferred embodiment, the optical pumping source 1 is a laser diode providing optical pumping excitation energy in the form of a single square wave pulse having a low power, preferably less than 1,000 peak Watts and a time duration of tens to several hundred microseconds. In yet another embodiment, the optical pumping source is one or more vertical-cavity surface-emitting lasers (VCSEL).

The optical pumping source 1 is optically connected to the laser media 5. In one embodiment, for example as shown in FIG. 1 and FIG. 2, the optical pumping source 1 is positioned along the optical axis 13. In an alternate embodiment, the optical pumping source 1 is positioned outside of, preferably normal to, the optical axis 13, preferably adjacent to the laser media 5, for example as shown in FIG. 3 and FIG. 4. In yet another embodiment, the optical pumping source 1 is optically connected to the laser media 5 via one or more optical fibers. Preferably, the pumping source 1 is positioned whereby the pumping excitation energy produced by the pumping source 1 is perpendicular to the optical axis 13.

The High Reflectivity Mirror (HR) 3

The high reflectivity mirror (HR) 3 is reflective to the atomic optical emission of the laser media 5. In one embodiment, the high reflectivity mirror (HR) 3 is transparent to the pumping excitation energy. The high reflectivity mirror (HR) 3 allows pumping excitation energy emitted from the optical pumping source 1 in the coaxial pumping configuration to pass through, while reflecting the intracavity atomic optical emission of the laser media 5. Preferably, the high reflectivity mirror (HR) 3 comprises undoped YAG, fused silica, sapphire or a combination thereof, preferably further comprising one or more thin film optical coatings deposited onto one face.

Preferably, the high reflectivity mirror (HR) 3 is a transparent optical media such as fused silica, or sapphire having a coating that is reflective to the atomic optical emission of the laser media, and that is transparent to the pumping excitation energy. More preferably, the high reflectivity mirror (HR) 3 is fused silica having a coating that is reflective to the atomic optical emission of the laser media, and that is transparent to the pumping excitation energy. In one embodiment, the high reflectivity mirror (HR) 3 comprises a plurality of coatings preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $A_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof.

In one embodiment, the high reflectivity mirror (HR) 3 is deposited as an optical coating onto the face of either the laser media 5 or the Q-switch 7 to define the optical cavity. In another embodiment the high reflectivity mirror (HR) 3 material has a large thickness where one side is bonded directly to the laser media 5 (or Q-switch 7) and the other side has the optical coating deposited directly on to it to define the optical cavity. By varying the thickness of the high reflectivity mirror (HR) material one can tune the length of the optical cavity and to help remove heat that the pumping excitation energy deposits into the face of the laser media 5 or Q-switch 7. When the high reflectivity mirror (HR) material has a significant thickness between the laser media 5 (or Q-switch 7) and the high reflectivity (HR) 3 optical coating, optical distortions caused by thermal lensing within the laser are reduced. The length of the cavity dictates the output pulsewidth and can be tuned to provide a pulsewidth that is most appropriate for a particular application.

The Laser Media 5

The laser media 5 is made of a material that emits an atomic optical emission when exposed to the pumping excitation energy. The laser media 5 is preferably made of one of the materials described in Koechner, W., Bass, M., "Solid State Lasers: A Graduate Text" Springer, New York, 2003 hereby fully incorporated by reference. The laser media 5 is generally a host material that is doped. The host materials are preferably glasses, or crystals of oxides, garnets, vanadates, fluorides, or a combination thereof. The Glasses are preferably doped with Nd, Er, or Yb. Oxides such as sapphire are preferably doped with Ti. The Garnets are preferably Yttrium Aluminum Garnet Y3Al5O12 (YAG), Gadolinium Gallium Garnet $Gd_3Ga_5O_2$ (GGG), and Gadolinium Scandium Aluminum Garnet $Gd_3Sc_2Al_3O_{12}$ (GSGG) and are preferably doped with rare earths such as Nd, Tm, Er, Ho, Yb. The Vanadates or Yttrium Orthovanadate (YVO4) are preferably doped with Nd. The Fluorides or Yttrium Fluoride (YLiF4) are preferably doped with Nd. The laser media 5 is preferably Nd:YAG (neodymium doped yttrium aluminium garnet), Nd:Glass (neodymium-doped glass), Nd:YLF (neodymium doped yttrium lithium fluoride), Nd:YVO4 (Yttrium Vanadate), Er:Glass (Erbium doped glass), Yb:YAG (ytterbium doped yttrium aluminium garnet), Alexandrite, Ti:Sapphire (Titanium sapphire), or a combination thereof. In the preferred embodiment the laser media 5 is Nd:YAG having about 0.5% atomic weight of Nd, which will emit an atomic optical emission at about 1064 nm.

The dopant level of the laser media 5 is preferably low to improve performance. Lowering the dopant concentration affects the overall output by improving the beam overlap efficiency (side pumped), improving the penetration depth (end pumped), improving the absorption depth of the optical pumping excitation energy, reducing thermal lensing losses, and reducing losses due to ASE (Amplified Spontaneous Emission). This leads to a more uniform pumped gain profile as well as more uniformly distributed thermal stresses which lessen the effects of thermal lensing. The reduction of dopant concentration lowers the gain of the material slightly but offers larger energy storage capacity in return.

Preferably, one or more coatings are used to reduce optical, thermal or a combination thereof stresses in the laser media 5. In a preferred embodiment, the laser media 5 comprises CR:YAG; Nd:YAG, or a combination thereof positioned between a first undoped YAG layer coating and a second undoped YAG layer coating along the optical axis.

The Q-Switch 7

The Q-Switch 7 is made of a material with a variable attenuation, which is reduced after optical stimulation from the lasing energy. The Q-switch 7 preferably comprises Li:F or Cr:YAG. The Q-switch 7 preferably comprises Cr:YAG (chromium doped yttrium aluminum garnet), when the lasing species is Nd, having enough Cr such that the small signal transmission of the atomic optical emission is in the range of 10-60%. The Q-switch 7 is positioned next to the laser media 5 and between the high reflectivity mirror (HR) 3 and the output coupler (OC) 9, FIG. 1 depicts one embodiment where the Q-switch 7 is positioned between the output coupler (OC) 9 and the laser media 5. In an alternate embodiment, as shown in FIG. 2, the Q-switch 7 is positioned between the high reflectivity mirror (HR) 3 and the laser media 5

The Output Coupler (OC) 9

The output coupler (OC) 9 is optically connected to the output lens along the optical axis 13. The output coupler (OC) 9 partially reflects the atomic optical emission of the laser media 5, preferably less than 50% of the atomic optical emission of the laser media 6 is reflected. In a preferred embodiment, the output coupler (OC) 9 reflects about 20-50% of the atomic optical emission of the laser media 5. Preferably, the output coupler (OC) 9 is fused silica, sapphire, undoped YAG, or a combination thereof, preferably further comprising a plurality of optical coatings deposited onto one face, preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $Al_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof. In the alternative, the output coupler (OC) 9 is another optical glass that is transparent to the atomic optical emission of the laser media, has a high optical damage threshold, and can receive an appropriate optically reflective coating.

In one embodiment, the output coupler (OC) 9 is deposited as an optical coating onto the face of either the laser media 5 or the Q-switch 7 to define the optical cavity. In another embodiment the output coupler (OC) 9 material has a large thickness where one side is bonded directly to the laser media (or Q-switch) and the other side has the optical coating deposited directly on to its opposing face to define the optical cavity. By varying the thickness of the partially reflecting mirror material one can tune the length of the optical cavity and/or to help remove heat that the pumping excitation energy deposits into the laser media 5 or Q-switch 7. When the output coupler (OC) mirror material has a significant thickness between the laser media 5 (or Q-switch 7) and the output coupler (OC) 9 optical coating it reduces optical distortions caused by thermal lensing within the laser. The output coupler (OC) 9 material preferably does not interact with either the pump energy or the atomic optical emission of the laser media 5 and is preferably used as a heat transfer media to reduce heat concentrations within the laser media 5 (or Q-switch 7). The length of the cavity dictates the output pulse width and can be tuned to provide a pulse width that is most appropriate for a particular application.

The Output Lens 11

The output lens 11 focuses the lasing energy. In the preferred embodiment, the output lens 11 is a piano-convex lens, preferably having a focal length of about 1-5 centimeters. Preferably, the output lens 11 is fused silica, sapphire, undoped YAG, or some other material that is transparent to the lasing energy, has an appropriate index of refraction, and has a high optical damage threshold. In another embodiment the output lens is a Bi-convex lens. Preferably, the output lens 11 has an anti-reflection coating.

A Means for Detecting Atomic Optical Emission of the Laser Media

Figure 5:
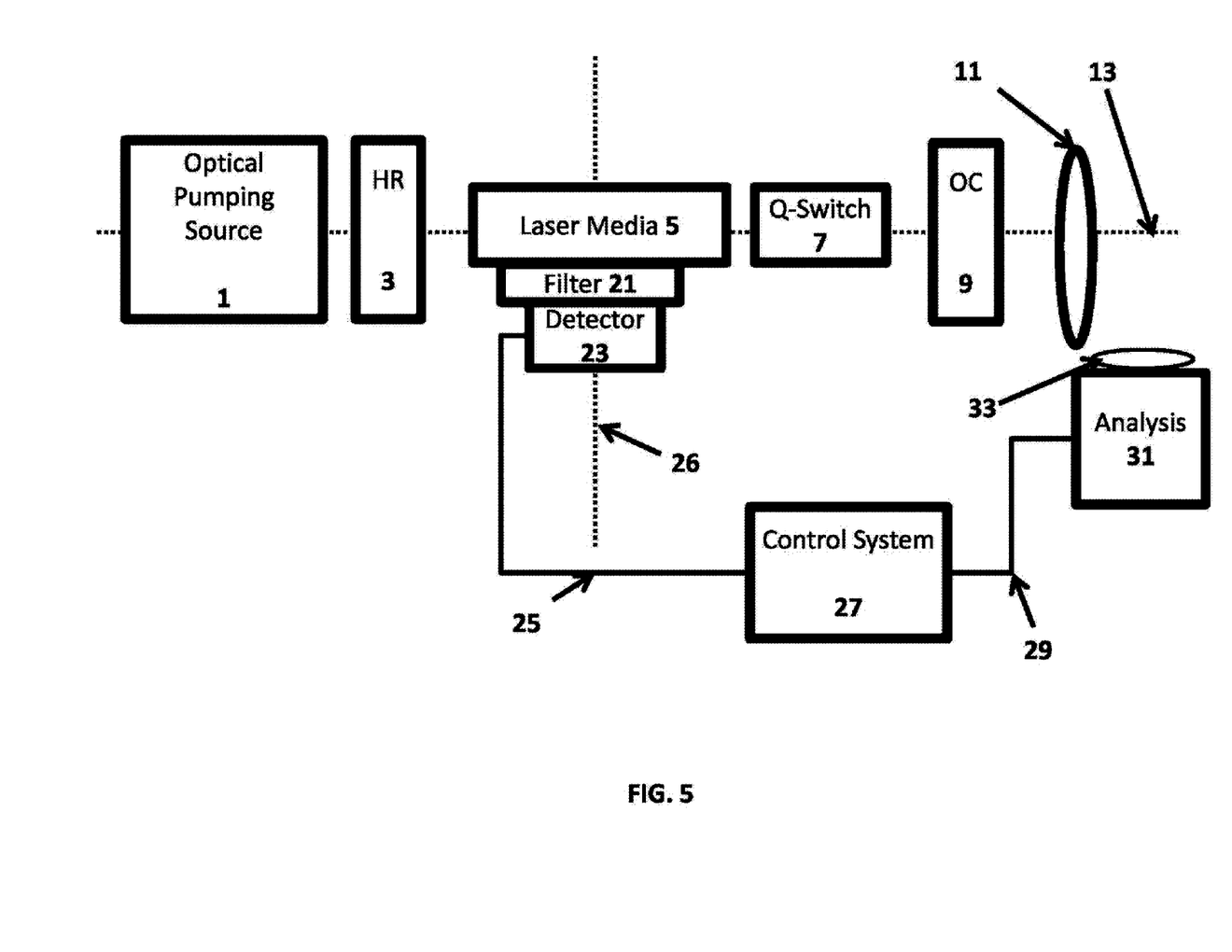
FIG. 5 depicts an overview of one embodiment of a device for Laser Based Analysis using a Passively Q-Switched Laser whereby the means for detecting atomic optical emission of the laser media comprises a filter and a photo-detector optically connected to the laser media.
Figure 6:
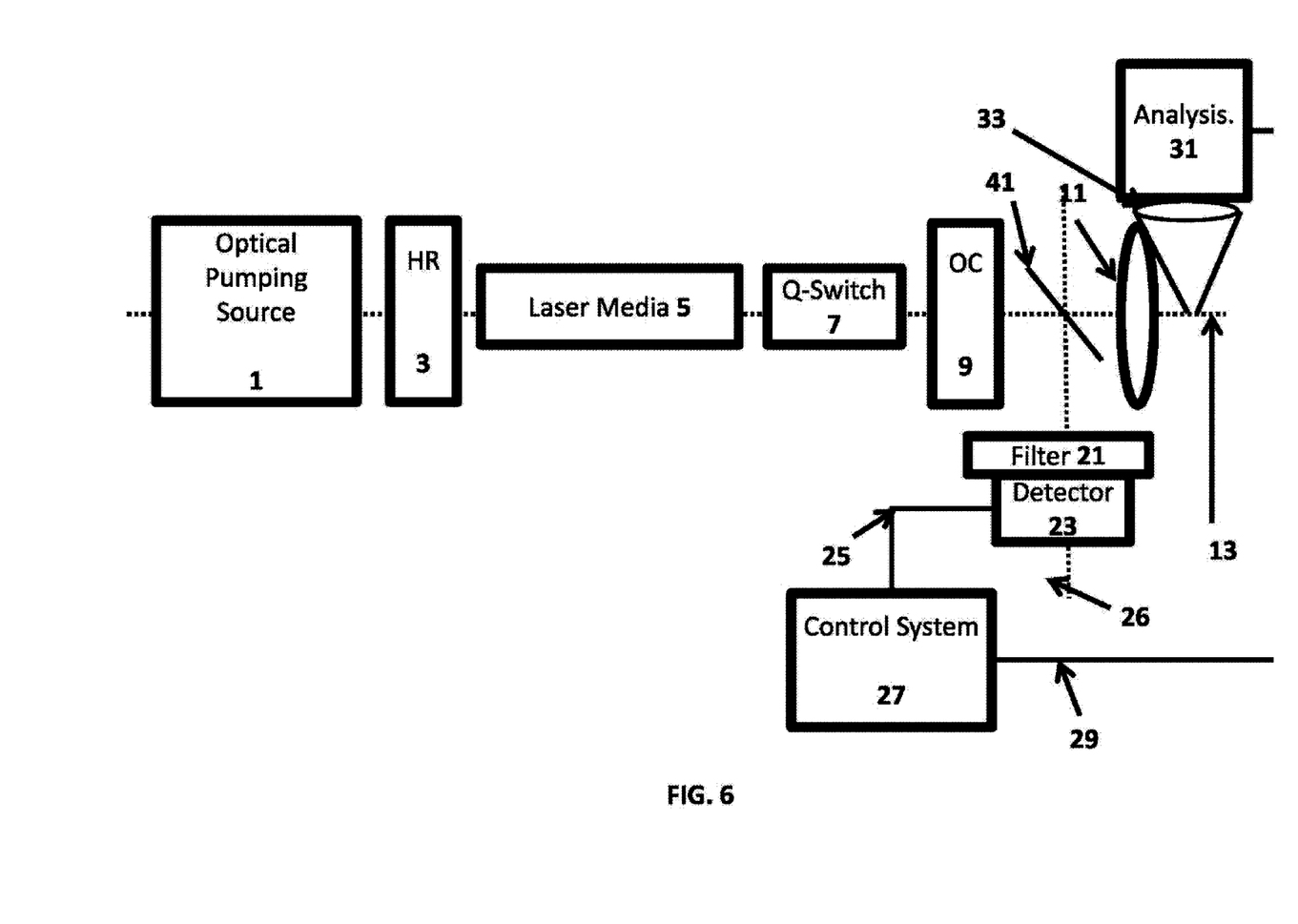
FIG. 6 depicts an overview of one embodiment of a device for Laser based Analysis using a Passively Q-Switched Laser whereby the means for detecting atomic optical emission of the laser media comprises a beam splitter at the output of the output coupler (OC) directing a portion of the laser emission to a filter and a photo-detector.
Figure 7:
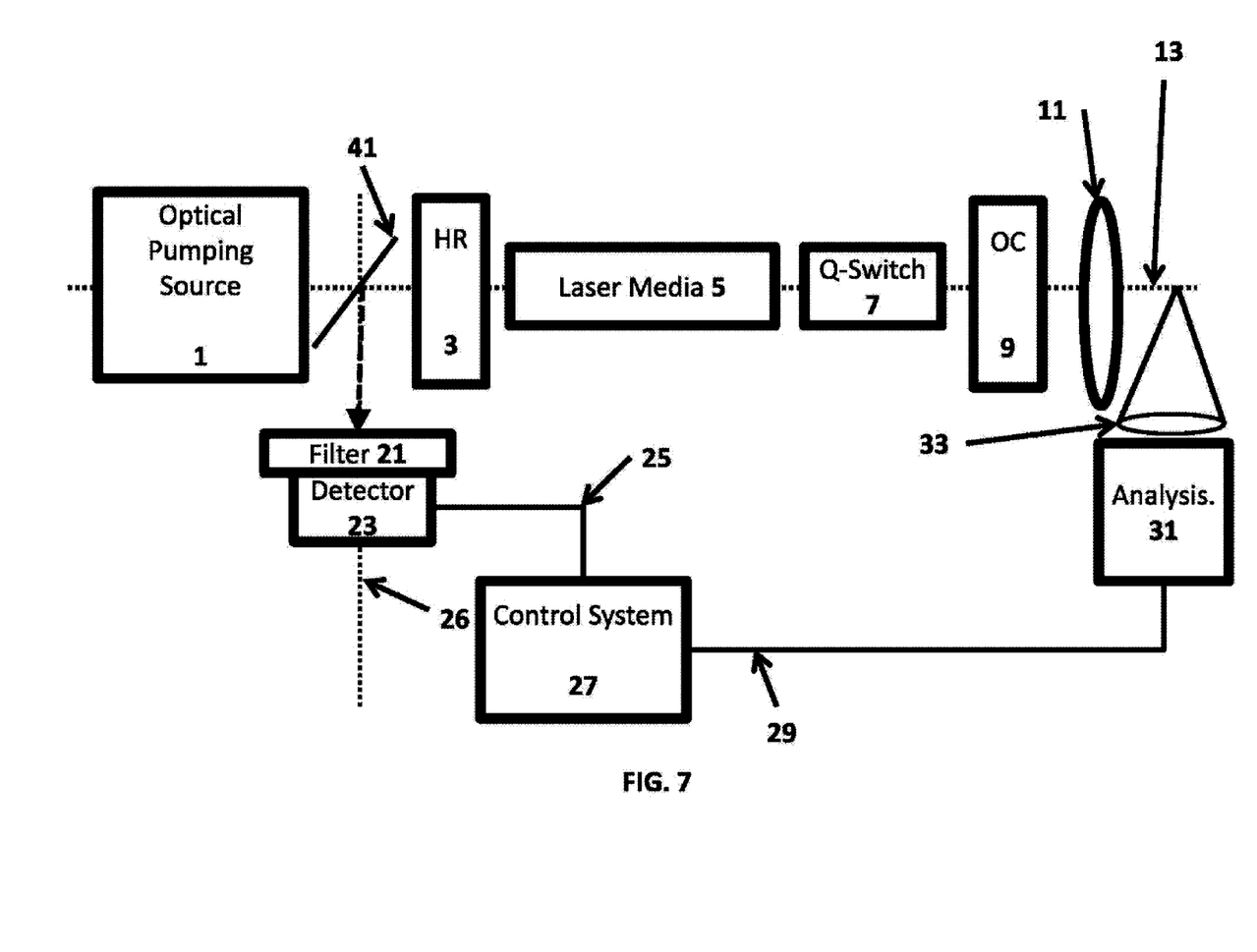
FIG. 7 depicts an overview of one embodiment of a device for Laser based Analysis using a Passively Q-Switched Laser whereby the means for detecting atomic optical emission of the laser media comprises a beam splitter at the output of the optical pumping source directing a portion of the laser emission to a filter and a photo-detector.

The means for detecting atomic optical emission of the laser media comprises a filter and a light detector. A filter is positioned between the light detector and the laser media 5 to filter out light that is not atomic optical emission of the laser media 5. The filter is designed to eliminate the transmission of the pump energy or any other excited state emission that is different from the lasing output wavelength. The filter and light detector are designed to detect leakage of the atomic optical emission of the laser media that is emitted in all directions from the high energy lasing process. Preferably, one or more electronic devices are used to determine precise timing of the operation of the laser media 5, as described in the various embodiments listed below. Various embodiments are depicted in FIGS. 5-7 and are described below.

FIG. 2

FIG. 2 depicts an overview of one embodiment of a device for Laser based Analysis using a Passively Q-Switched Laser with an alternate positioning of the Q-switch 7. This embodiment is the same as shown in FIG. 1 and described above with the exception that the positioning of the Q-switch 7 and the laser media 5 are switched. Therefore, in this embodiment, the Q-switch 7 is positioned between the laser media 5 and the high reflectivity mirror (HR) 3. In this embodiment the Q-switch 7 is preferably Lithium Fluoride (Li:F) or other material that does not attenuate pumping excitation energy passing through.

FIG. 3

FIG. 3 depicts an overview of one embodiment of a device for Laser based Analysis using a Side-pumped, Passively Q-Switched Laser. This embodiment is the same as shown in FIG. 1 and described above with the exception that the Optical pumping source 1 is positioned adjacent to the laser media 5 and outside of the optical axis 13. Preferably, the pumping source 1 is positioned whereby the pumping excitation energy produced by the pumping source 1 is perpendicular to the optical axis 13. The embodiment shown in FIG. 3 also depicts a plurality of optical pumping source 1, although any number, including 1 may be used.

FIG. 4

FIG. 4 depicts an overview of one embodiment of a device for Laser based Analysis using a Side-pumped, Passively Q-Switched Laser with an alternate positioning of the Q-switch. This embodiment is the same as shown in FIG. 2 (the Q-switch 7 positioned between the laser media 5 and the high reflectivity mirror (HR) 3) as described above with the exception that the Optical pumping source is positioned adjacent to the laser media 5 and outside of the optical axis 13. Preferably, the pumping source 1 is positioned whereby the pumping excitation energy produced by the pumping source 1 is perpendicular to the optical axis 13. The embodiment shown in FIG. 4 also depicts a plurality of optical pumping source 1, although any number, including 1 may be used.

FIG. 5

FIG. 5 depicts an overview of one embodiment of a device for Laser based Analysis using a Passively Q-Switched Laser whereby the means for detecting atomic optical emission of the laser media 5 comprises a filter 21 and a photo-detector 23 optically connected to the laser media 5. This embodiment is the same as shown in FIG. 1 and described above with additional depiction of a filter 21, a photo detector 23, a first wire 25, a control system 27, a second wire 29, analysis electronics 31 and an analysis lens 33. As shown, the filter 21 is positioned between the laser media 5 and the detector 23 along a detector axis 26. Although the detector axis 26 is depicted as perpendicular to said optical axis 13, the detector 26 may have any orientation as long as it is not the same axis as the optical axis 13. The control system 27 is connected to the photo detector 23 via the first wire 25. The control system 27 is connected to the analysis electronics 31 via the second wire 29. The analysis lens 33 is positioned between the output of the output lens 11 and the analysis electronics 31 and is intended to focus light emission for the analysis electronics 31. Preferably, the photo detector 23 and the analysis electronics 31 combined at least perform the function of a spectrometer, whereby the intensity of one or more wavelengths of light are determined and conveyed to the user.

The Filter 21

The filter 21 is any material that at least attenuates light that is not atomic optical emission of the laser media 5. In one preferred embodiment, the filter 21 is an interference filter. In one embodiment, the filter 21 blocks or reflects the majority of light, including atomic optical emission of the laser media 5, to prevent damage, atomic optical emission detections, or a combination of at the detector 23. Preferably, the filter 21 is made of an absorbing glass which absorbs the pumping excitation energy and transmits at least some of the atomic optical emission of the laser media 5.

In a preferred embodiment, the filter 21 is a bandpass filter comprised of laminated layers of absorbing glass with coatings of vacuum deposited metallic blocker such as silver which reflects most light and a vacuum deposited thin film partial reflector that transmits a narrow bandwidth of light centered at the atomic optical emission of the laser media 5 with a bandwidth of approximately +/−2 nm. The partially reflecting thin film is preferably constituted primarily of alternating layers of low index of refraction materials whose presence or absence can be used to tune the reflectivity and the center wavelength to the desired area of operation. The thin films are preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $Al_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof.

The Photo Detector 23

The photo detector 23 is a device that is capable of detecting atomic optical emission of the laser media 5. Preferably, the photo detector 23 is a photomultiplier, a photoresistor, or a photodiode with the necessary electronics to connect to the control system 27. As the filter 21 attenuates light that is not atomic optical emission of the laser media 5, light reaching the photo detector 23 will substantially be atomic optical emission of the laser media 5. Preferably, the system is designed to account for any light that is not atomic optical lasing emission of the laser media 5 light that reaches the system, for example by setting a threshold value for intensity of light reaching the photo detector 23 before atomic optical emission of the laser media 5 is considered as detected.

In one embodiment, a resistor with a known resistance and a photo resistor are connected in series across a voltage source. In another embodiment, one or more voltage comparators, Analog-to-digital converters (ADC), transistors, amplifiers, or a combination thereof are used to connect the photo detector 23 to the control system 27. For example, in one embodiment, the output of the photodiode is electrically connected to the input of a current-to-voltage amplifier circuit. In another embodiment, a photodiode is electrically connected to a voltage source in revere bias with a current detector, whereby a change in current is related to a change in light intensity detected.

The Control System 27

The control system 27 is any device capable of reading the output from the photo detector 23 and controlling the analysis electronics 31. The control system 27 preferably comprises a processor, computer, application specific integrated controller (ASIC), microcontroller, CPU, or a combination thereof. In one embodiment the control system 27 is an AMEGA128 as sold by ATMEL.

The Analysis Electronics 31

The analysis electronics 31 are any electronics used to analyze a specimen using the apparatus described herein. In a preferred embodiment, the analysis electronics 31 are electronics used to perform laser-induced breakdown spectroscopy (LIBS). Laser-induced breakdown spectroscopy (LIBS) uses a highly energetic laser pulse as the excitation source and an optical spectrometer as an analyzer. The laser is focused to form a plasma, which atomizes and excites samples. Preferably, LIBS is used to analyze any matter regardless of its physical state, be it solid, liquid or gas. Because all elements emit light of characteristic frequencies when excited to sufficiently high temperatures, LIBS can (in principle) detect all elements, limited only by the power of the laser as well as the sensitivity and wavelength range of the spectrometer and its detector.

Preferably, in embodiments using LIBS, the analysis electronics 31 operates by focusing the laser onto a small area at the surface of the specimen; when the atomic optical emission of the laser media 5 is discharged it ablates a very small amount of material, in the range of nanograms to picograms, which generates a plasma plume with temperatures preferably in excess of 10,000 K. Preferably, during data collection, preferably after local thermodynamic equilibrium is established, plasma temperatures range from 5,000-20,000 K. At the high temperatures during the early plasma, the ablated material dissociates (breaks down) into excited ionic and atomic species. During this time, the plasma emits a continuum of radiation which does not contain any useful information about the species present, but within a very small timeframe the plasma expands at supersonic velocities and cools. At this point the characteristic atomic emission lines of the elements can be observed. The delay between the emission of continuum radiation and characteristic radiation is on the order of 1 to 10 μs and this is why it is necessary to temporally gate the detector. As the photo detector 23 detects the precise time of the atomic optical emission of the laser media 5, the control system 27 is able to determine the time that the analysis should be performed and turn on an optical gate to collect only the characteristic radiation.

In the alternative, other laser-based analytical techniques may be used using the same or similar hardware. For example, techniques using the vibrational spectroscopic technique of Raman spectroscopy, and the fluorescence spectroscopic technique of laser-induced fluorescence (LIF). Preferably for embodiments using Raman or LIF, the detection of atomic optical lasing emissions by the photo detector 23 is simultaneous with output of the atomic optical lasing emission.

The Analysis Lens 33

The analysis lens 33 focuses light from the atomic optical emission of the laser media 5 and preferably any resulting light emissions for detection by the analysis electronics 31. In the preferred embodiment, the analysis lens 33 is a piano-convex or a bi-convex lens. In one embodiment, the analysis lens 33 has a focal point of about 1-5 centimeters.

FIG. 6

FIG. 6 depicts an overview of one embodiment of a device for Laser based Analysis using a Passively Q-Switched Laser whereby the means for detecting atomic optical emission of the laser media 5 comprises a beam splitter at the output of the output coupler (OC) directing a portion of the atomic optical emission of the laser media to a filter and a photo-detector. This embodiment is the same as shown in FIG. 5 and described above with the exception that the photo detector 23 and corresponding filter 21 are positioned at the output of the output coupler (OC) 9 instead of at the laser media 5 as shown in FIG. 5. Therefore, in this embodiment, the beam splitter 41 is positioned between the output coupler (OC) 9 and the output lens 11 along the optical axis 13. In this embodiment, atomic optical emission of the laser media 5 passes through the output coupler (OC) 9 and into a beam splitter 41. The optical filter 21 is positioned between the beam splitter 41 and said optical detector 23 along a detector axis 26. Although the detector axis 26 is depicted as perpendicular to said optical axis 13, the detector 26 may have any orientation as long as it is not the same axis as the optical axis 13. The beam splitter 41 passes a portion of the atomic optical emission of the laser media 5 through the filter 21 and to the photo detector 23. This embodiment may be preferable as the detector 23 will most likely be closer to sample, presumably at the output of the output lens 11.

The Beam Splitter 41

The beam splitter 41 is any device which is capable of partially reflecting atomic optical emission of the laser media 5 through the filter 21 to the photo detector 23. Preferably, the beam splitter 41 is a partial reflector orientated to specularly reflect a portion of the atomic optical emission of the laser media 5 through the filter 21 to the photo detector 23. Preferably, the beam splitter 41 is made of fused silica. The beam splitter 41 preferably comprises a thin glass slide or a partially reflecting dielectric thin film coating on an optical substrate. Partially reflecting thin film coatings are preferably made of Silicon, Titanium, Tantalum, Zirconium, Hafnium, Scandium, Niobium, oxides thereof, fluorides thereof or combinations thereof. More preferably, the coatings preferably comprise materials with various indices of refraction for example as $Al_2O_3$, $Ta_2O_5$, $SiO_2$, $TiO_2$, $CaF_2$, $ZrO_2$, $BeO_2$, $MgF_2$, $LaF_3$ and $AlF_3$ or combinations thereof.

In a preferred embodiment, the beam splitter 41 is made of fused silica with vacuum deposited thin films deposited on the primary face to tune the operating wavelength and the reflectivity and an anti-reflection coating on the downstream face to improve transmission and reduce undesirable optical effects such as additional off-axis reflections and ghosting of the primary optical signal. The partially reflecting thin film is preferably constituted primarily of alternating layers of low index of refraction materials whose presence or absence can be used to tune the reflectivity and the center wavelength to the desired area of operation. The thin films are preferably made up of oxides of Silicon, Titanium, Tantalum, Zirconium, Hafnium, Scandium, Niobium or combinations thereof. The anti-reflection coatings preferably comprise a vacuum deposited thin film of Magnesium Fluoride.

FIG. 7

FIG. 7 depicts an overview of one embodiment of a device for Laser based Analysis using a Passively Q-Switched Laser whereby the means for detecting atomic optical emission of the laser media 5 comprises a beam splitter 41 positioned between the optical pumping source 1 and said high reflectivity mirror (HR) 3 along the optical axis 13 directing a portion of the leakage atomic optical emission of the laser media 5 to a filter 21 and a photo-detector 23. This embodiment is the same as shown in FIG. 6 and described above with the exception that the beam splitter 41 and corresponding filter 21 are positioned between the optical pumping source 1 and said high reflectivity mirror (HR) 3 along the optical axis 13 instead of at the output coupler (OC) 9 as shown in FIG. 6. The optical filter 21 is positioned between the beam splitter 41 and said optical detector 23 along a detector axis 26. Although the detector axis 26 is depicted as perpendicular to said optical axis 13, the detector 26 may have any orientation as long as it is not the same axis as the optical axis 13. In this embodiment, atomic optical emission of the laser media 5 passes through the high reflectivity mirror (HR) 3 as leakage and onto a beam splitter 41. The beam splitter 41 reflects a portion of the atomic optical emission of the laser media 5 through the filter 21 and to the photo detector 23. The beam splitter is preferably constructed in such a way as to have a low reflectivity for the pump energy and a high reflectivity for the leakage atomic optical lasing emission.

FIG. 8

Figure 8:
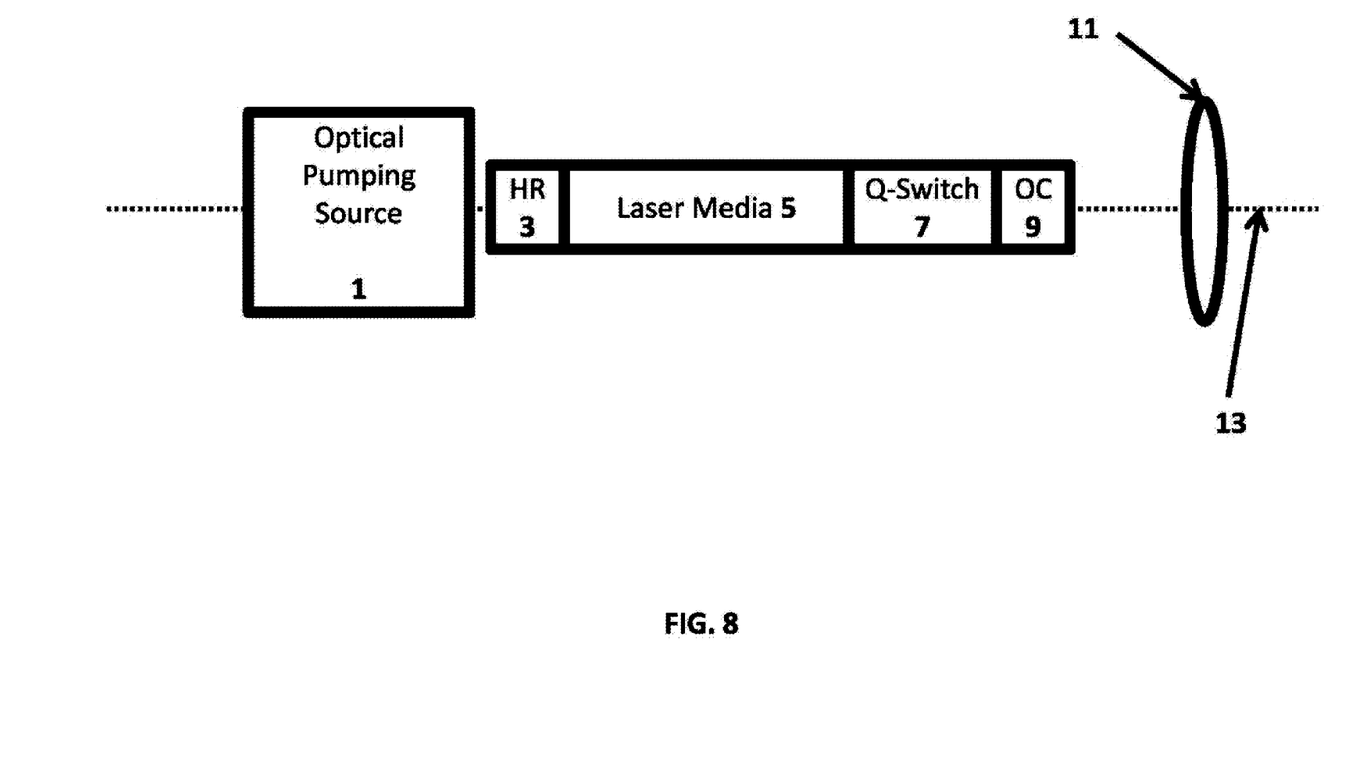
FIG. 8 depicts an overview of one embodiment of a device for Laser Based Analysis using a monolithic, Passively Q-Switched Laser.

FIG. 8 depicts an overview of one embodiment of a device for Laser Based Analysis using a monolithic, Passively Q-Switched Laser. This embodiment is the same as shown in FIG. 1 and described above with the exception that the high reflectivity mirror (HR) 3, the laser media 5, the Q-switch 7, and the output coupler (OC) 9 are depicted as forming one monolithic material. In this embodiment, the high reflectivity mirror (HR) 3 and the output coupler (OC) 9 are thin film dielectric coatings on the outward faces of the laser media 5 and the Q-switch 7, respectively. As discussed above, the Q-switch 7 and the laser media 5 are positioned between the high reflectivity mirror (HR) 3 and the output coupler (OC) 9 along the optical axis 13 in any order. Therefore, in one embodiment, the position of the laser media 5 in FIG. 8 is switched with the location of the laser media 5.

In a preferred embodiment, the high reflectivity mirror (HR) 3 is an optical coating deposited onto undoped YAG, fused silica, sapphire or a combination thereof on the laser media 5; the Q-switch 7 is comprised of Li:F or Cr:YAG and is bonded thereof to the laser media 5; and the output coupler (OC) 9 is an optical coating deposited onto fused silica, sapphire, undoped YAG, or a combination thereof on the laser media 5.

FIG. 9

Figure 9:
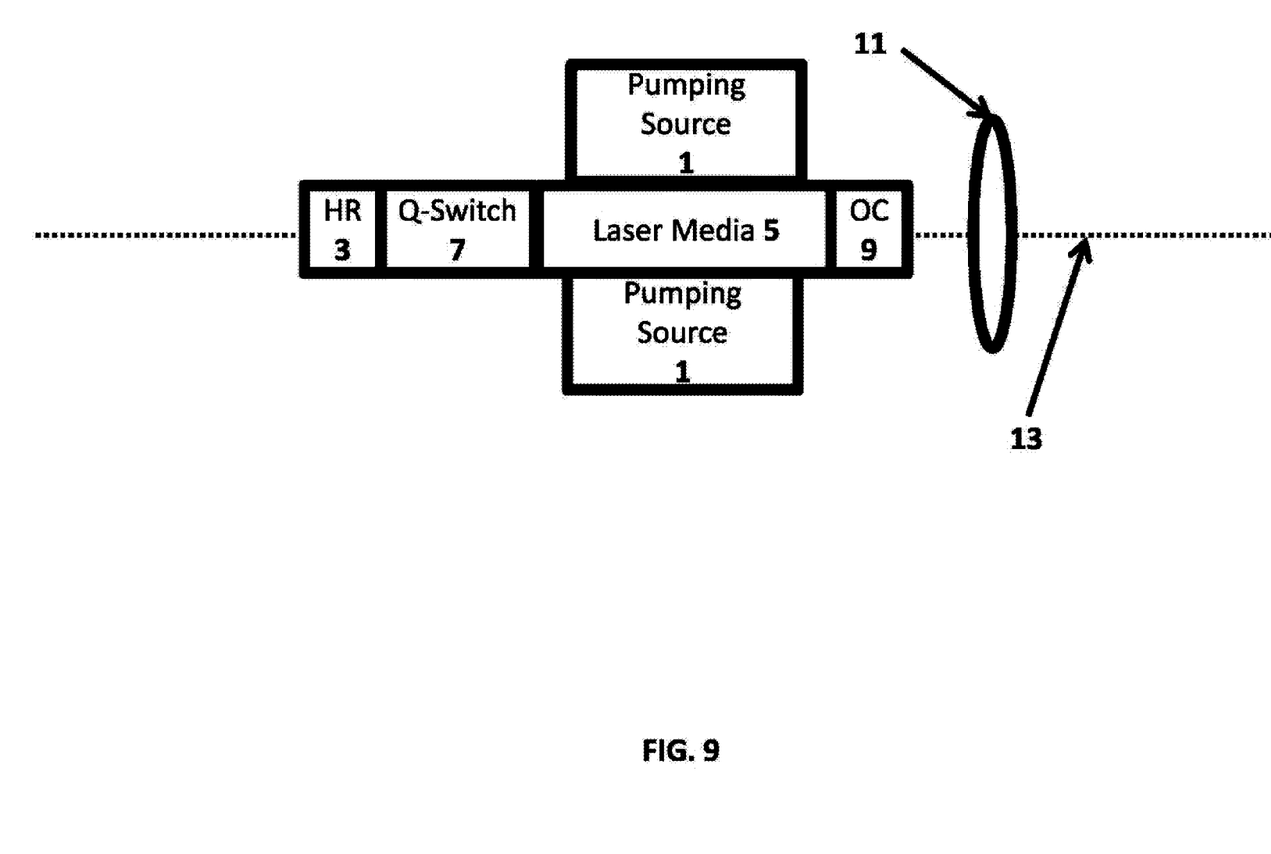
FIG. 9 depicts an overview of one embodiment of a device for Laser Based Analysis using a monolithic, side-pumped, Passively Q-Switched Laser.

FIG. 9 depicts an overview of one embodiment of a device for Laser Based Analysis using a monolithic, side-pumped, Passively Q-Switched Laser. This embodiment is the same as shown in FIG. 4 and described above with the exception that the high reflectivity mirror (HR) 3, the laser media 5, the Q-switch 7, and the output coupler (OC) 9 are depicted as forming one monolithic material. In this embodiment, the high reflectivity mirror (HR) 3 and the output coupler (OC) 9 are thin film dielectric coatings on the outward faces of the laser media 5 and the Q-switch 7, respectively. As discussed above, the Q-switch 7 and the laser media 5 are positioned between the high reflectivity mirror (HR) 3 and the output coupler (OC) 9 along the optical axis 13 in any order. Therefore, in one embodiment, the position of the laser media 5 in FIG. 8 is switched with the location In a preferred embodiment, the high reflectivity mirror (HR) 3 is an optical coating deposited onto undoped YAG, fused silica, sapphire or a combination thereof on the laser media 5; the Q-switch 7 is comprised of Li:F or Cr:YAG and is bonded thereof to the laser media 5; and the output coupler (OC) 9 is an optical coating deposited onto fused silica, sapphire, undoped YAG, or a combination thereof on the laser media 5.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

All publications and patent documents cited in this application are incorporated by reference in their entirety for all purposes to the same extent as if each individual publication or patent document were so individually denoted.

Any element in a claim that does not explicitly state "means for" performing a specified function, or "step for" performing a specific function, is not to be interpreted as a "means" or "step" clause as specified in 35 U.S.C. §112, ¶6. In particular, the use of "step of" in the claims herein is not intended to invoke the provisions of 35 U.S.C. §112, ¶6.

The invention claimed is:

1. A device for Laser based Analysis using a Passively Q-Switched Laser comprising:
    a) an optical pumping source, a high reflectivity mirror (HR), a laser media, a Q-switch, an output coupler (OC), an output lens, a means for detecting atomic optical emission from said laser media, a control system, and analysis electronics;
    b) said high reflectivity mirror (HR), said laser media, said Q-switch, said output coupler (OC) and said output lens positioned along an optical axis;
    c) said optical pumping source optically connected to said laser media;
    d) said optical pumping source creating a pumping excitation energy;
    e) said laser media made of a material that emits an atomic optical emission when exposed to said pumping excitation energy;
    f) said high reflectivity mirror (HR) reflective to said atomic optical emission of said laser media;
    g) said laser media and said Q-switch positioned between and optically connected to said high reflectivity mirror (HR) and said output coupler (OC) along said optical axis;
    h) said output coupler (OC) optically connected to said output lens along said optical axis;
    i) said means for detecting atomic optical emission of said laser media comprising an optical filter and an optical detector; and said optical filter optically connected to said laser media and said optical detector;

j) said optical filter optically connecting said optical detector to said atomic optical emission of said laser media;

k) said optical filter filtering at least a portion of said pumping excitation energy;

l) said control system connected to said optical detector and said analysis electronics;

m) said analysis electronics optically connected to said output lens; and n) said optical filter is a bandpass filter allowing the transmission of atomic optical emissions from said laser media to pass to said optical detector while attenuating frequencies outside of its pass-band range.

2. The device for Laser based Analysis using a Passively Q-Switched Laser of claim 1 whereby:

a) said optical pumping source, said high reflectivity mirror (HR), said laser media, said Q-switch, said output coupler (OC) and said output lens are all positioned along said optical axis.

3. The device for Laser based Analysis using a Passively Q-Switched Laser of claim 2 whereby:

a) said Q-switch is positioned between said laser media and said output coupler (OC); and b) said Q-switch comprises CR:YAG.

4. The device for Laser based Analysis using a Passively Q-Switched Laser of claim 2 whereby:

a) said Q-switch is positioned between said high reflectivity mirror (HR) and said laser media; and b) said Q-switch comprises Li:F.

5. The device for Laser based Analysis using a Passively Q-Switched Laser of claim 1 whereby:

a) said optical pumping source is positioned adjacent to said laser media outside of said optical axis.

6. The device for Laser based Analysis using a Passively Q-Switched Laser of claim 5 whereby:

a) said Q-switch is positioned between said laser media and said output coupler (OC).

7. The device for Laser based Analysis using a Passively Q-Switched Laser of claim 5 whereby:

a) said Q-switch is positioned between said high reflectivity mirror (HR) and said laser media.

8. The device for Laser based Analysis using a Passively Q-Switched Laser of claim 1 whereby:

a) said laser media comprises Nd:YAG.

9. The device for Laser based Analysis using a Passively Q-Switched Laser of claim 1 whereby:

a) said high reflectivity mirror (HR) comprises undoped YAG, fused silica, sapphire or a combination thereof further comprising one or more thin film optical coatings deposited onto one face.

10. The device for Laser based Analysis using a Passively Q-Switched Laser of claim 1 whereby:

a) said output coupler (OC) comprises undoped YAG fused silica, sapphire or a combination thereof further comprising one or more thin film optical coatings deposited onto one face.

11. The device for Laser based Analysis using a Passively Q-Switched Laser of claim 1 whereby a) said laser media comprises CR:YAG; Nd:YAG, or a combination thereof positioned between a first undoped YAG coating and a second undoped YAG coating along said optical axis.

12. The device for Laser based Analysis using a Passively Q-Switched Laser of claim 1 whereby:

a) said optical pumping source is one or more Vertical-cavity surface-emitting lasers (VCSEL).

13. The device for Laser based Analysis using a Passively Q-Switched Laser of claim 1 whereby:

a) said optical pumping source is one or more laser diodes.

14. The device for Laser based Analysis using a Passively Q-Switched Laser of claim 1 whereby said means for detecting atomic optical emission of said laser media comprises:

a) said optical filter positioned between said laser media and said optical detector;

b) said optical filter and said optical detector positioned along a detector axis; and c) said detector axis different from said optical axis.

15. The device for Laser based Analysis using a Passively Q-Switched Laser of claim 1 whereby said means for detecting atomic optical emission of said laser media comprises:

a) a beam splitter;

b) said beam splitter positioned between said output coupler (OC) and said output lens along said optical axis; and c) said optical filter positioned between said beam splitter and said optical detector along an axis different from said optical axis.

16. The device for Laser based Analysis using a Passively Q-Switched Laser of claim 1 whereby said means for detecting atomic optical emission of said laser media comprises:

a) a beam splitter;

b) said beam splitter positioned between optical pumping source and said high reflectivity mirror (HR) along said optical axis; and c) said optical filter positioned between said beam splitter and said optical detector along an axis different from said optical axis.

17. The device for Laser based Analysis using a Passively Q-Switched Laser of claim 3 whereby:

a) said laser media comprises Nd:YAG;

b) said high reflectivity mirror (HR) comprises undoped YAG, fused silica, sapphire or a combination thereof;

c) said output coupler (OC) comprises undoped YAG fused silica, sapphire or a combination thereof;

d) said optical pumping source is one or more Vertical-cavity surface-emitting lasers (VCSEL);

e) said optical filter positioned between said laser media and said optical detector;

f) said optical filter and said optical detector positioned along a detector axis; and g) said detector axis different from said optical axis.

18. The device for Laser based Analysis using a Passively Q-Switched Laser of claim 4 whereby:

a) said laser media comprises Nd:YAG;

b) said high reflectivity mirror (HR) comprises undoped YAG, fused silica, sapphire or a combination thereof;

c) said output coupler (OC) comprises undoped YAG fused silica, sapphire or a combination thereof;

d) said optical pumping source is one or more Vertical-cavity surface-emitting lasers (VCSEL);

e) said optical filter positioned between said laser media and said optical detector;

f) said optical filter and said optical detector positioned along a detector axis; and g) said detector axis different from said optical axis.

19. The device for Laser based Analysis using a Passively Q-Switched Laser of claim 5 whereby:

a) said laser media comprises Nd:YAG;

b) said high reflectivity mirror (HR) comprises undoped YAG, fused silica, sapphire or a combination thereof;

c) said output coupler (OC) comprises undoped YAG fused silica, sapphire or a combination thereof;

d) said optical pumping source is one or more Vertical-cavity surface-emitting lasers (VCSEL);
e) said optical filter positioned between said laser media and said optical detector;
f) said optical filter and said optical detector positioned along a detector axis; and
g) said detector axis different from said optical axis.

* * * * *